United States Patent
Vetter et al.

(10) Patent No.: US 6,229,314 B1
(45) Date of Patent: May 8, 2001

(54) TESTING HYPODERMIC SYRINGES PRIOR TO AUTOMATED FILLING

(75) Inventors: Helmut Vetter, deceased, late of Ravensburg; by Bianca Vetter, heir, Deggenhausertal-Untersiggingen; by Udo J. Vetter, heir, Ravensburg; by Cornelia Vetter-Kerkhof, heir, München; Udo J. Vetter; Stefan Mossig, both of Ravensburg, all of (DE)

(73) Assignee: Arzneimittel GmbH Apotheker Vetter & Co. Ravensburg, Ravensburg (DE)

( * ) Notice: Subject to any disclaimer, the term of this patent is extended or adjusted under 35 U.S.C. 154(b) by 0 days.

(21) Appl. No.: 09/252,459

(22) Filed: Feb. 18, 1999

(30) Foreign Application Priority Data

Feb. 19, 1998 (DE) ............................................... 198 06 971

(51) Int. Cl.$^7$ ................................................... G01N 27/00
(52) U.S. Cl. ........................................................... 324/559
(58) Field of Search ............................. 324/559; 422/129, 422/63, 67, 73, 82.08; 436/43, 63, 172, 174, 175; 110/250, 346, 236; 60/50; 604/21, 51; 435/173.6

(56) References Cited

U.S. PATENT DOCUMENTS

| 3,623,210 | 11/1971 | Shields . |
| 5,389,069 | * 2/1995 | Weaver ................................. 604/21 |

FOREIGN PATENT DOCUMENTS 3215289    11/1989   (DE) .

* cited by examiner

*Primary Examiner*—Safet Metjahic
*Assistant Examiner*—E P LeRoux
(74) *Attorney, Agent, or Firm*—Herbert Dubno; Andrew Wilford

(57) ABSTRACT

A syringe subassembly comprised of a tubular syringe body having a front end provided with a forwardly projecting needle and fitted over the needle with a cap of a dielectric material is tested by juxtaposing an outer electrode with the cap, juxtaposing an inner electrode with the needle, applying a high electrical voltage across the electrodes, monitoring current flow between the electrodes, and rejecting the syringe subassembly if the monitored current flow exceeds a predetermined level. The cap is normally made of a plastic and has a higher dielectric constant than the gas surrounding the subassembly in the test station, normally air.

20 Claims, 4 Drawing Sheets

TESTING HYPODERMIC SYRINGES PRIOR TO AUTOMATED FILLING

FIELD OF THE INVENTION

The present invention relates to the automated filling of hypodermic syringes. More particularly this invention concerns a system for testing the syringes prior to such filling.

BACKGROUND OF THE INVENTION

A standard prefilled hypodermic syringe has a tubular body whose front end is fitted with a needle or cannula, whose rear end is blocked by a slidable plunger, and which is fitted over the needle with a protective cap. Normally such a syringe is filled from the back, that is the assembled body, needle, and cap are held in an upright position and an automated device fills the required medicament into the body, whereupon the plunger is installed.

The subassembly comprised of the body, needle, and end cap is typically made up in a high-speed machine. The needle is fitted to the front end of the body, then the cap is fitted over the needle, all as mentioned by automatic equipment at relatively high speed.

A common problem is that the needle is set so that it is not perfectly aligned with the centerline of the body. Thus when the cap is installed the needle can touch, poke into, or even poke through the cap. This clearly creates a potentially unsanitary condition in that bacteria can enter the otherwise sealed assembly through the hole in the cap created by the misaligned needle.

The standard procedure is simply to have a worker visually examine the needle assemblies before final packaging and to pick out and discard any bad subassemblies. Such a system is, clearly, labor intensive and cannot be guaranteed to catch every bad needle subassembly, especially when the needle does not project all the way through the wall of the cap or, after poking through it, has somehow withdrawn inside to leave a hole that is nearly impossible to see. Finally it is in fact desirable to reject any subassemblies where the needle is simply too close to the cap, within say 0.1 mm to 0.2 mm, as during subsequent transport and handling the needle might well come into contact with the cap wall and pierce it.

OBJECTS OF THE INVENTION

It is therefore an object of the present invention to provide an improved system for checking hypodermic-needle assemblies prior to filling.

Another object is the provision of such an improved system for checking hypodermic-needle assemblies prior to filling which overcomes the above-given disadvantages, that is which surely and positively detects any needle subassemblies where the needle has poked into or through the cap wall and even where the needle is simply too close to the inner surface of the cap.

SUMMARY OF THE INVENTION

A syringe subassembly comprised of a tubular syringe body having a front end provided with a forwardly projecting needle and fitted over the needle with a cap of a dielectric material is tested according to the invention by juxtaposing an outer electrode with the cap, juxtaposing an inner electrode with the needle, applying a high electrical voltage across the electrodes, monitoring current flow between the electrodes, and rejecting the syringe subassembly if the monitored current flow exceeds a predetermined level. The cap is normally made of a plastic and has a higher dielectric constant than the gas surrounding the subassembly in the test station, normally air.

Thus this system does not rely on the appearance of the subassembly at all, but actually tests for a breach in the cap or an inadequate spacing between the needle and the inside surface of the cap. It can test the subassemblies at a faster rate and with more accuracy than has hitherto been possible.

According to the invention the inner electrode is juxtaposed with the conductive metallic needle inside the body, since the needle usually projects backward somewhat into the space defined by the hollow body. More particularly the inner electrode is directly contacted with the needle inside the body, although the method of this invention will work if the inner electrode is merely very closely juxtaposed with the needle.

The inner electrode is an elongated pin and is formed with a longitudinally throughgoing passage. This allows this pin to be used to flush out the body by injecting a gas through the passage into the body during and/or after the test.

Normally according to the invention four or six such subassemblies are simultaneously juxtaposed with a single outer electrode and with respective inner electrodes and current flows between the inner electrodes and the outer electrode are individually monitored. Such gang testing is facilitated when the outer electrode is elongated and of U-section and the subassemblies are juxtaposed with it by being moved longitudinally along the outer electrode.

The high electrical voltage according to the invention is a direct current voltage of about 10 kV, preferable 12 kV to 14 kV.

The apparatus has according to the invention a holder for retaining the subassembly in a testing station, an outer electrode juxtaposed with the cap in the station, an inner electrode juxtaposable with the needle, a current supply for applying a high electrical voltage across the electrodes, and a monitoring system for detecting current flow between the electrodes so that if the monitored current flow exceeds a predetermined level the subassembly can be rejected. The inner electrode is a pin insertable into the syringe body and formed with a longitudinally forwardly open passage. Thus it is possible to pass a gas through the passage to flush out or sterilize the body.

For safest operation and reduced possibility of unwanted arcing the pin is mainly insulated and only has an exposed uninsulated tip. In addition so that the system can test several subassemblies at one time the outer electrode is of U-section, and separate inner electrodes with monitoring systems are used.

The outer electrode can be cup-shaped to be complementarily to the cap.

In order to prevent an electrostatic charge from being left on the needle subassembly, which charge could atomize a liquid subsequently poured into it and coat upper regions of the inner surface of the body that should remain dry, means is provided for discharging such an electrostatic charge. This means can generate an ion cloud around the subassembly. The mist can be stationary with the needle subassemblies being passed through it as they leave the testing apparatus.

Such a discharging unit includes discharge electrodes energized at about 5 kV of alternating current. These electrodes can be arrayed complementarily in a circle around the subassembly and holder. The ionizing head can be of other, for instance rectangular, square, or oval, shape. Furthermore the discharge unit can include nozzles alternating with the discharge electrodes and emitting jets of air for moving the discharge mist.

BRIEF DESCRIPTION OF THE DRAWING

The above and other objects, features, and advantages will become more readily apparent from the following description, reference being made to the accompanying drawing in which.

SPECIFIC DESCRIPTION

Figure 1A:
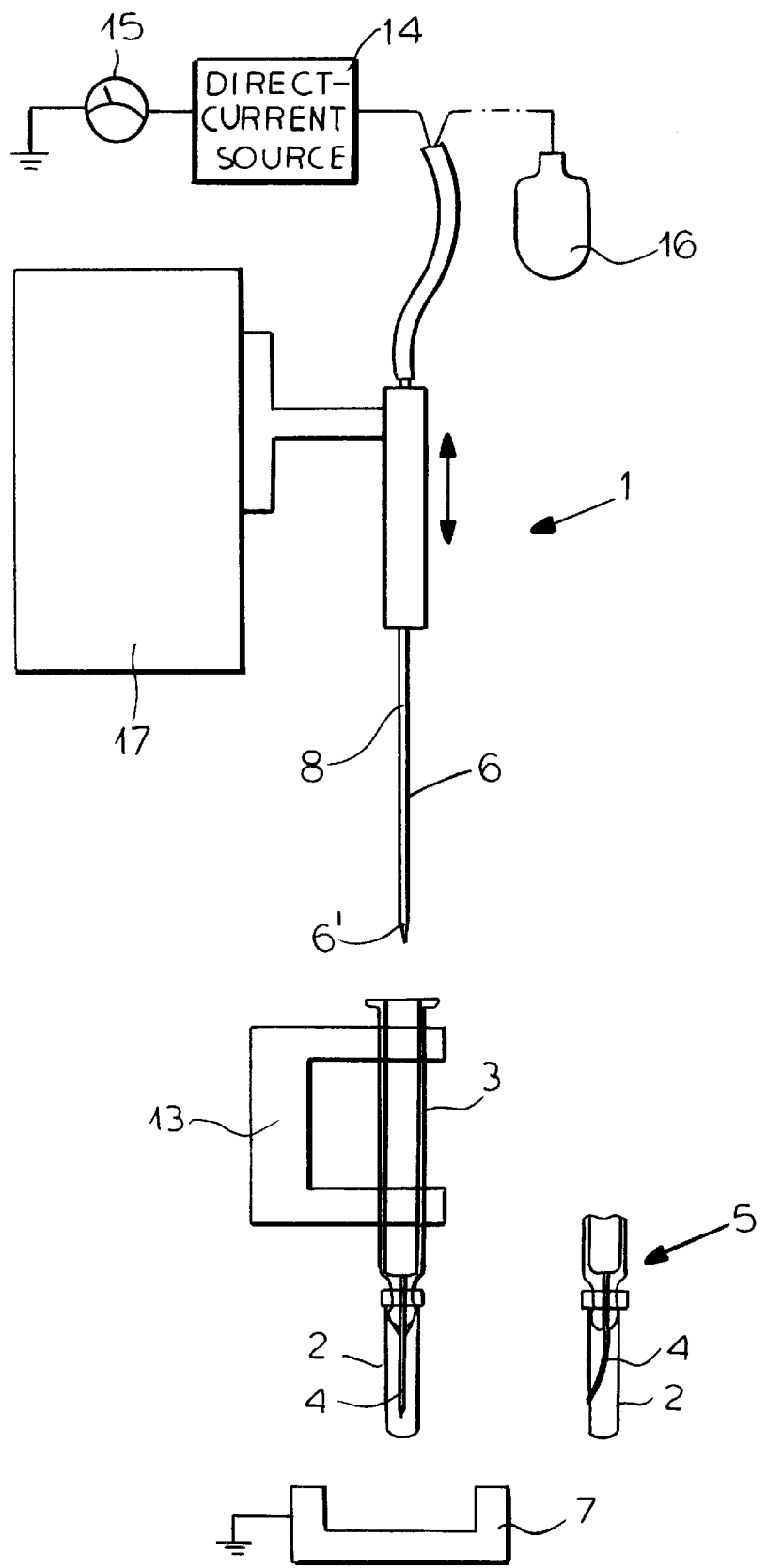
FIGS. 1A and 1B are largely schematic side views of the apparatus for carrying out the method of this invention in two different positions.
Figure 1B:
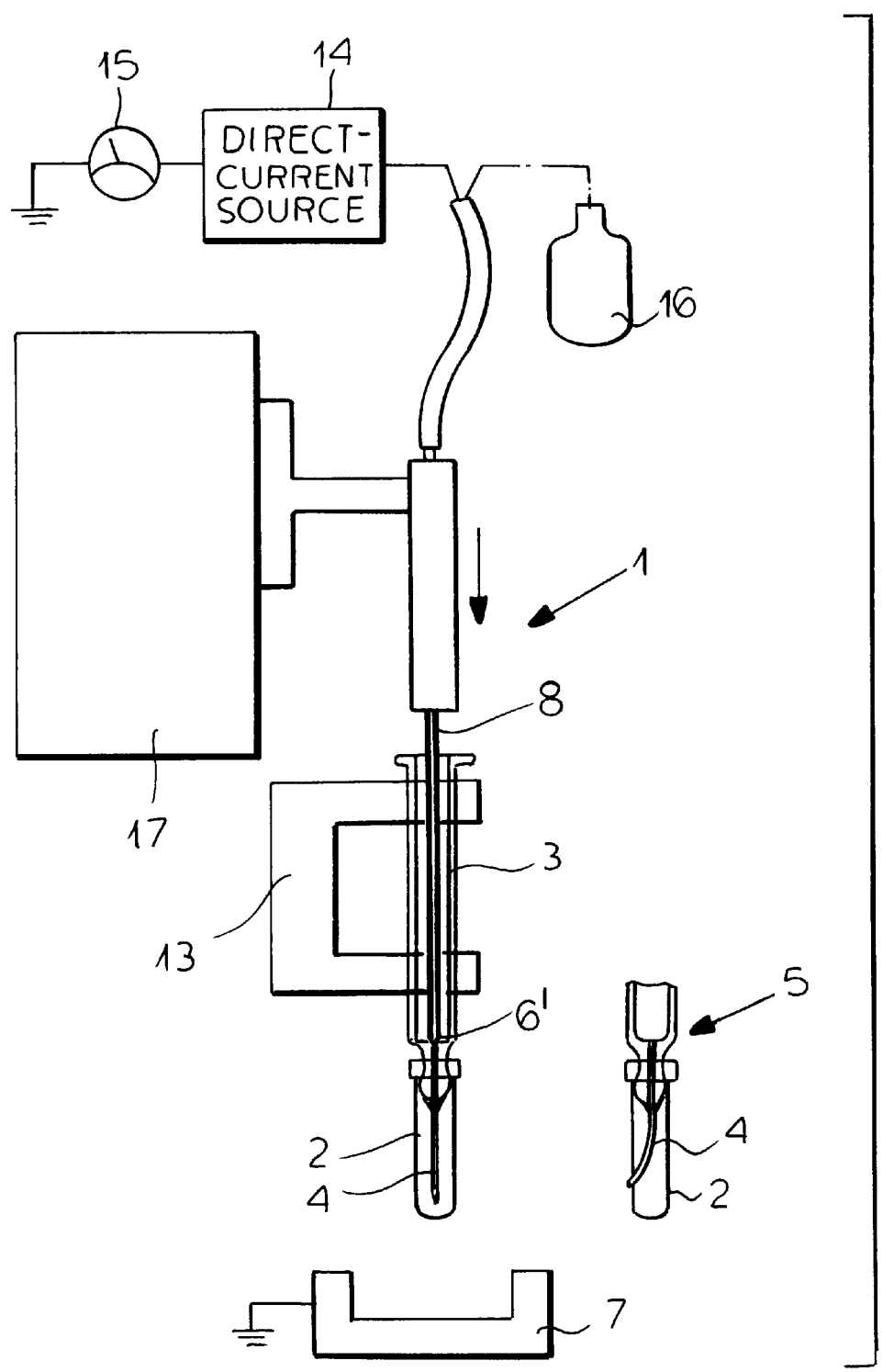

As seen in FIGS. 1A and 1B a plurality of test stations 1, of which only one is shown, each have a holder 13 in which is mounted a standard glass or plastic syringe body 3 fitted with a needle 4 surrounded by a standard plastic cap 2. Normally the needle 4 is centered in the cap 2, but as shown for the rejected needle subassembly 5, the needle 4 can poke into or through the wall of the transparent cap 2. In fact if the tip of the needle 4 is within 0.1 mm to 0.2 mm of the inner surface of the cap 2, the subassembly should be rejected.

According to the invention an inner electrode 6 formed as an elongated tubular pin covered with insulation 8 except at its tip 6' can be displaced by an actuating assembly 17 longitudinally downward from the position shown in FIG. 1A into the body 3 until the tip 6' touches or is very closely juxtaposed with the upper rear end of the needle 4 to the position shown in FIG. 1B. In addition a U-shaped outer electrode 7 that is grounded is positioned underneath the cap 2, the electrode 7 being upwardly concave so as to be generally complementary to the cap 2. A source 14 of direct current in excess of 10 kV and a monitoring system shown schematically at 15 are also connected between ground and the metallic pin 6. In addition in order to sterilize and/or flush out the tube 3, a supply 16 of an appropriate gas can be connected to the rear end of the hollow pin 16 to inject this gas into the very base of the body 3.

Thus it is possible to establish a large voltage differential between the needle 2 and the counter electrode 7. Since the plastic cap 2 and body 3 are normally a much better dielectric than the air between the needle 4 and the electrode 7, if the needle 4 is poked through the cap 2 or the cap 2 has a hole, or even if the needle 4 is too closely juxtaposed with the inner surface of the cap 2, there will be a measurable current flow that can be detected by the means 15. When this current flow exceeds a predetermined limit, the subassembly is rejected; otherwise it is moved along the production line to the stations where it is filled and fitted with a plunger.

Figure 2:
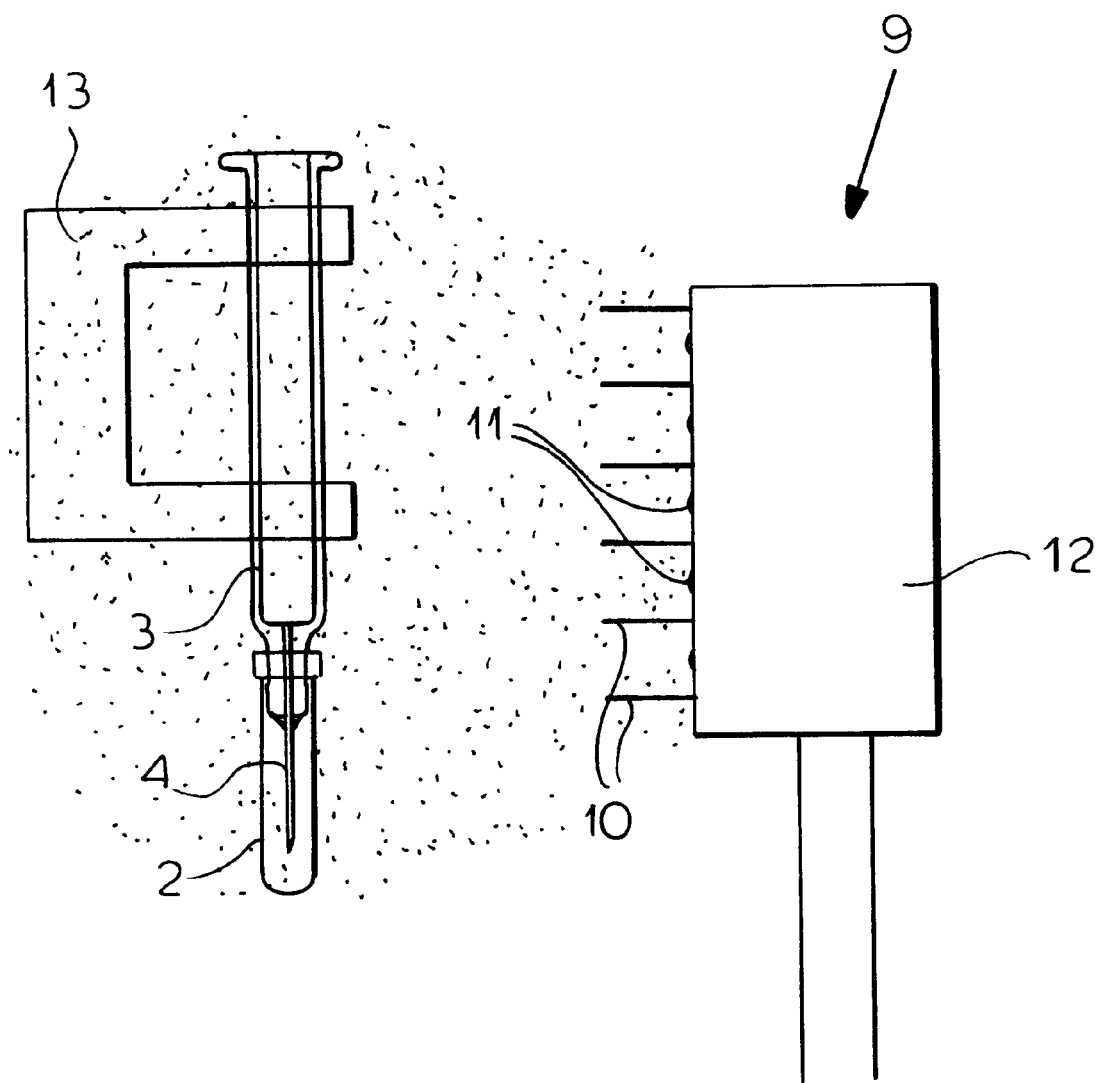
FIG. 2 is a side view illustrating a step of the method of the invention.

FIG. 2 shows how immediately downstream of the testing station 1 is a discharging station 9 having an ionizing head 12 carrying a plurality of discharge electrodes 10 energized at about 5 kV of alternating current and interleaved with nozzles 11 that blow an ion cloud around the good needle subassemblies. The ionization of the cloud produced by these electrodes 10 eliminates any charge the prior testing step may have left on the needle subassembly.

Figure 3:
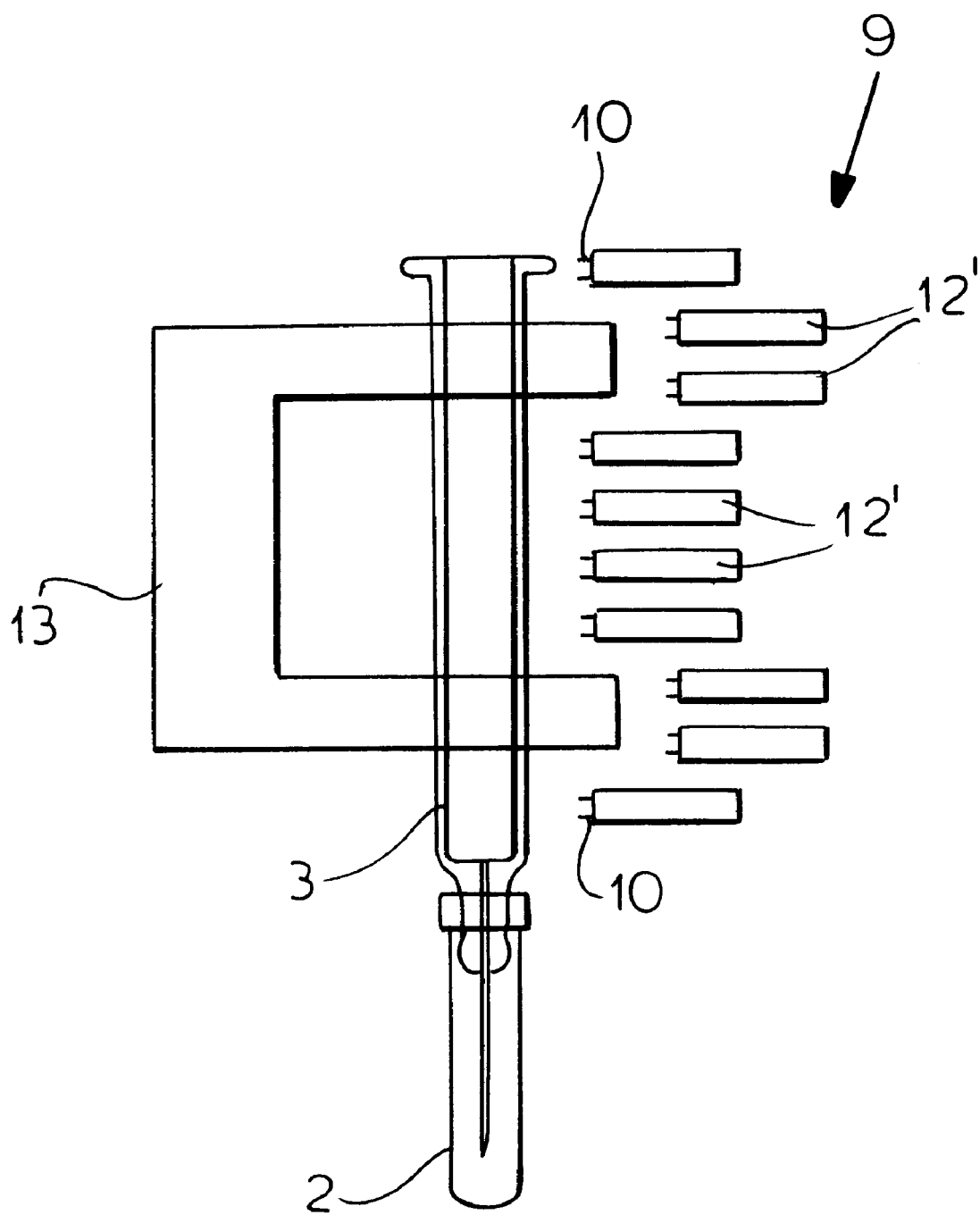
FIG. 3 is a view like FIG. 2 illustrating another aspect of the apparatus according to the invention.

In FIG. 3 an arrangement is shown which is similar but where a multiplicity of small ionizing heads 12' are used that are arrayed to fit complementarily around the needle body 3 and holder 13. Each such head 12' carries two small electrodes 10 energized as described above.

We claim:

1. A method of testing a syringe subassembly comprised of a tubular syringe body having a front end provided with a forwardly projecting needle and fitted over the needle with a cap of a dielectric material, the method comprising the steps of:

juxtaposing an outer electrode with the cap;
juxtaposing an inner electrode with the needle;
applying a high electrical voltage across the electrodes;
monitoring current flow between the electrodes; and
rejecting the syringe subassembly if the monitored current flow exceeds a predetermined level.

2. The syringe-testing method defined in claim 1 wherein the inner electrode is juxtaposed with the needle inside the body.

3. The syringe-testing method defined in claim 2 wherein the inner electrode is directly contacted with the needle inside the body.

4. The syringe-testing method defined in claim 2 wherein the inner electrode is elongated and formed with a longitudinally throughgoing passage, the syringe-testing method further comprising the step of injecting a gas through the passage into the body.

5. The syringe-testing method defined in claim 1 wherein a plurality of such subassemblies are simultaneously juxtaposed with a single outer electrode and with respective inner electrodes and current flows between the inner electrodes and the outer electrode are individually monitored.

6. The syringe-testing method defined in claim 5 wherein the outer electrode is elongated and of U-section and the subassemblies are juxtaposed with it by being moved longitudinally along the outer electrode.

7. The syringe-testing method defined in claim 1 wherein the high electrical voltage is a direct current voltage of about 10 kV.

8. The syringe-testing method defined in claim 1, further comprising the step of:

disconnecting the high electrical voltage from the electrodes; and thereafter
discharging the needles of any electrostatic charge.

9. An apparatus for testing a syringe subassembly comprised of a tubular syringe body having a front end provided with a forwardly projecting needle and fitted over the needle with a cap of a dielectric material, the apparatus comprising:

means for holding the subassembly in a testing station;

an outer electrode juxtaposed with the cap in the station;

means for juxtaposing an inner electrode with the needle;

supply means for applying a high electrical voltage across the electrodes; and monitoring means for detecting current flow between the electrodes, whereby if the monitored current flow exceeds a predetermined level the subassembly is rejected.

10. The syringe-testing apparatus defined in claim 9 wherein the inner electrode is a pin insertable into the syringe body.

11. The syringe-testing apparatus defined in claim 10 wherein the pin is formed with a longitudinally forwardly open passage, the apparatus further comprising means for passing a gas through the passage.

12. The syringe-testing apparatus defined in claim 10 wherein the pin is mainly insulated and only has an exposed uninsulated tip.

13. The syringe-testing apparatus defined in claim 9 wherein the counter electrode is of U-section.

14. The syringe-testing apparatus defined in claim 9 wherein the counter electrode is shaped complementarily to the cap.

15. The syringe-testing apparatus defined in claim 9 wherein the voltage is direct and at least 10 kV.

16. The syringe-testing apparatus defined in claim 9, further comprising means for discharging the subassembly of any electrostatic charge.

17. The syringe-testing apparatus defined in claim 16 wherein the discharging means generates an ion cloud around the subassembly.

18. The syringe-testing apparatus defined in claim 17 wherein the discharging means includes discharge electrodes energized at about 5 kV of alternating current.

19. The syringe-testing apparatus defined in claim 17 wherein the discharge electrodes are arrayed complementarily to the subassembly and holder.

20. The syringe-testing apparatus defined in claim 17 wherein the discharging means including cloud-moving nozzles alternating with discharge electrodes.

* * * * *